United States Patent [19]

Beylin et al.

[11] Patent Number: 4,689,423
[45] Date of Patent: Aug. 25, 1987

[54] PROCESS FOR THE PREPARATION OF 2,3,4,5-TETRAFLUOROBENZOYL ACETATES

[75] Inventors: Vladimir G. Beylin; Om P. Goel, both of Ann Arbor, Mich.

[73] Assignee: Warner-Lambert Company, Morris Plains, N.J.

[21] Appl. No.: 846,695

[22] Filed: Apr. 1, 1986

[51] Int. Cl.$^4$ ............................................. C07C 67/14
[52] U.S. Cl. ..................................... 560/51; 562/459; 562/496
[58] Field of Search ................... 560/51; 562/459, 496

[56] References Cited

FOREIGN PATENT DOCUMENTS 899399  7/1984  Belgium .
0106489  4/1984  European Pat. Off. .

OTHER PUBLICATIONS

Wierenga et al., *J. Org. Chem.*, vol. 44, No. 2, pp. 310–311, (1979).
Yakobson et al., *Thurnal Obshchei Khimii*, vol. 36, No. 1, pp. 139–142, Jan. 1966.

*Primary Examiner*—Werren B. Lone
*Assistant Examiner*—Vera C. Clarke
*Attorney, Agent, or Firm*—Elizabeth M. Anderson

[57] ABSTRACT

An improved process for the preparation of methyl 2,3,4,5-tetrafluorobenzoylacetate is described. The process is for intermediates that lead to trifluoroquinolinic acids which in turn are used to produce antibacterial agents of the difluoro quinolinecarboxylic acid type. The process runs at room temperature, uses a safe and inexpensive base, and can be conveniently scaled up for manufacturing purposes.

4 Claims, No Drawings

PROCESS FOR THE PREPARATION OF 2,3,4,5-TETRAFLUOROBENZOYL ACETATES

BACKGROUND OF THE INVENTION

The process of the present invention is a simplified method for preparing 2,3,4,5-tetrafluorobenzoylacetates. One advantage of the process is that it can be carried out at or above ambient temperatures using a safe, and inexpensive base which is commercially available as a dry powder. A further advantage is that this process can be scaled-up conveniently.

In contrast to the method of the present invention, a literature method (J. Org. Chem., 44:310–311 (1979), was found to be applicable to synthesize 2,3,4,5-tetrafluorobenzoyl acetates. However, this method required very low temperatures and large amounts of n-butyllithium solutions which are expensive and pyrophoric. In this process for the synthesis of β-ketoesters, malonic acid monethyl ester in tetrahydrofuran is treated by slow addition of n-butyl lithium at −30° C. to −5° C. to yield a heterogeneous mixture. The mixture is then cooled to −65° C. and treated with an acid chloride such as tetrafluorobenzoyl chloride.

The 2,3,4,5-tetrafluorobenzoyl acetic acid esters of the present invention of general formula

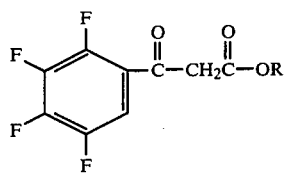

wherein R is a straight or branched alkyl of from one to four carbon atoms, are used in the preparation of trifluoroquinolinic acids of the general formula

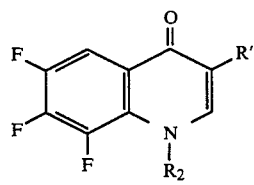

wherein R' is CN or COOR", in which R" is hydrogen or an alkyl of one to six carbon atoms or aralkyl, and $R_2$ is an alkyl of from one to three carbon atoms or a cycloalkyl of from three to six carbon atoms. These compounds are described in copending application Ser. No. 818,450 filed 1/13/86.

The trifluoroquinolinic acids are intermediates in the synthesis of compounds of the general formula

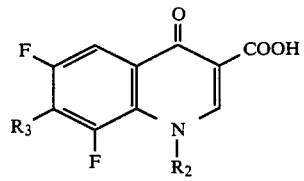

wherein $R_3$ is amino or cyclic amino; $R_2$ as described above, especially cyclopropyl.

Such compounds are found in Belgium Patent 899,399 which describes certain 7-piperazine-1-cyclopropyl-6,8-difluoro-1,4-dihydro-4-oxo-3-quinolinecarboxylic acids. U.S. Pat. No. 4,556,658 describes various 7-amino-1-cyclopropyl-6,8-difluoro-1,4-dihydro-4-oxo-3-quinolinecarboxylic acids. European Patent Publication 106,489 describes 7-cyclic amino-1-alkyl-6,8-difluoro-1,4-dihydro-4-oxo-3-quinolinecarboxylic acids.

The above compounds are useful as antibacterial agents.

The antibacterial compounds are prepared by displacement of a 7-fluoro atom from a compound of the formula

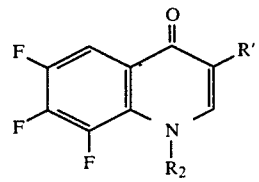

wherein R' is CN or COOR", in which R" is hydrogen or an alkyl of one to six carbon atoms or aralkyl, and $R_2$ is alkyl of one to three carbon atoms or cycloalkyl of three to six carbon atoms. This involves heating at reflux a compound of the above formula with an amine $R_3$ as described earlier, in the presence of at least one equivalent of a tertiary amine in a polar aprotic solvent.

SUMMARY AND DETAILED DESCRIPTION

The present invention is a greatly improved process for making tetrafluorobenzoyl acetic acid esters. These esters lead to the trifluoroquinolinic acids which are intermediates in the synthesis of difluoroquinoline-carboxylic acid which are in turn useful as antibacterials.

An essential feature of the present invention is the room temperature formation of sodium dimethylmalonate in a toluene-dimethylformamide (DMF) mixture as a nice fluid slurry which when reacted with an acid chloride such as tetrafluorobenzyl chloride leads to the formation of β-keto esters after hydrolysis. Other essential features of the invention are the use of a safe and inexpensive base, sodium methoxide, which is also commercially available as an anhydrous powder; mild to moderate reaction conditions throughout and the ease of scale-up for manufacturing purposes.

Scheme 1

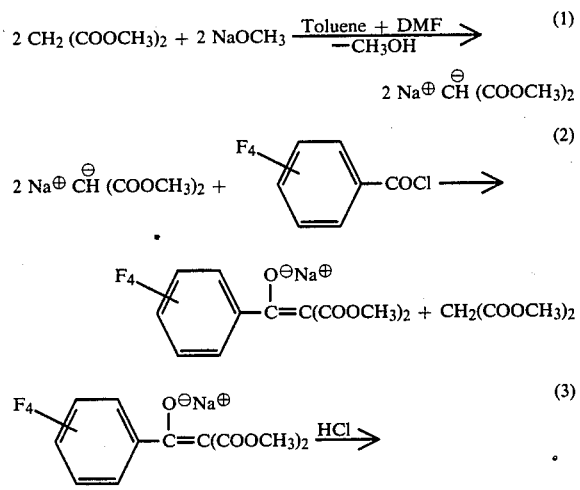

-continued
Scheme 1

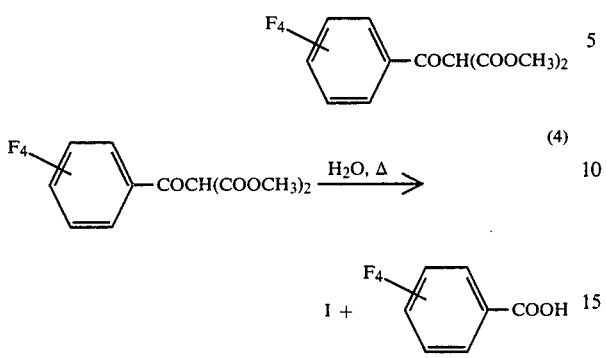

Step 1 of synthetic Scheme I is illustrative of the present invention.

In Step 1 a dialkylmalonate is treated with anhydrous sodium methoxide in toluene-DMF to produce a slurry of sodium dialkylmalonate.

The reaction in Step 1 is smooth and the toluenemethanol can be distilled out to give a fluid slurry of sodium dialkylmalonate. The fluid slurry and the smooth reaction make it possible to do large scale production of this process. Even without DMF, the reaction proceeds but a thick slurry is obtained which is difficult to handle on large scale.

Also in Step 1 the volume ratio of the toluene to DMF is from 30 to 1 to 70 to 1. Preferably the ratio is approximately 50 to 1.

In Step 2 the slurry of sodium dialkyl malonate is stirred with tetrafluorobenzoyl chloride to produce the corresponding acylation product, tetrafluorobenzoyldialkyl malonate. The two equivalent of sodium dialkyl malonate are needed since the acylation product also forms an enolate.

In Step 2 stirring is continued for from one to four hours. Preferably from two to three hours.

The temperature in Step 2 is from 10° to 30° C. Preferably the temperature is from 18° to 20° C.

In Step 3 the acylation product as described above is extracted into water and then acidified to form the tetrafluorobenzoyldialkyl malonate.

In Step 4 the dialkylmalonate is hydrolyzed to produce the compound of Formula I. The by-product is tetrafluorobenzoic acid which can be recycled by routine conversion to tetrafluorobenzoylchloride for Step 2.

The process of the present invention is for producing compound of formula

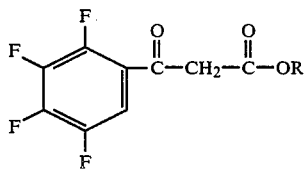

wherein R is a straight or branched alkyl of from one to four carbon atoms. The term alkyl includes, for example, methyl, ethyl, propyl, isopropyl, butyl, sec-butyl, isobutyl, tertiary-butyl, and the like. When R is other than methyl, use of sodium methoxide in Step 1 leads to a mixture of products wherein R has partially exchanged with the methyl group derived from sodium methoxide (alkoxide exchange). This, however, does not cause any difficulty as the R group is subsequently removed by hydrolysis to obtain antibacterial compounds of the formula

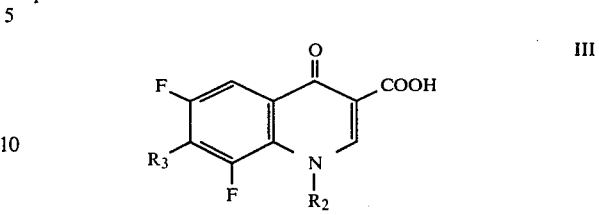

as described before.

A preferred embodiment of the present invention is the use of dimethylmalonate in Step 1.

Another preferred embodiment is the use of toluene with dimethylformamide in a volume ratio of approximately 50 to 1 in Step 1.

Still another preferred embodiment is the use of the base sodium methoxide in Step 1.

Yet another preferred embodiment is in the reaction temperature of from 18° to 20° C. in Step 2.

A particular embodiment is the process whereby the compound obtained is methyl 2,3,4,5-tetrafluorobenzoylacetate.

The 2,3,4,5-tetrafluorobenzoyl chloride used in Step 2 is prepared by known methods from tetrafluorobenzoic acid, for example. Tetrafluorobenzoic acid is in turn prepared by decarboxylation of tetrafluorophthalic acid at 145° C. as described in G. C. Yakobson, et al, in Zhurnal Obshchei Khimii, 36(1), pages 139–42 (1966) or as described in copending U.S. application Ser. No. 773,490 of Sept. 9, 1985, which involves heating tetrafluorophthalic acid with a base catalyst in a polar, aprotic solvent at a temperature of 90° to 140° C.

The following example is illustrative of the invention but is not meant to limit the invention in any way.

EXAMPLE 1

A 500 ml, three-necked flask was set up in a heating mantle and equipped with a mechanical stirrer, an equilibrating type addition funnel, a thermometer, an inert gas (argon or nitrogen) inlet, and a distillation head set for downward distillation. The flask was charged with 100 ml of toluene, 2 ml of dimethylformamide, and 2.84 g (0.0525 mol) of anhydrous sodium methoxide. The slurry was heated with stirring to 110° C., and dimethylmalonate (7.1 g, 0.0538 mol) was added dropwise from the addition funnel over 15 to 20 minutes. A total of 20 ml of distillate was collected at a vapor temperature of 50°–105° C. A fluid slurry was obtained. After five minutes at 105° C. (vapor), the mixture was cooled to 18°–20° C., and 5.3 g (0.025 mol) of 2,3,4,5-tetrafluorobenzoyl chloride was added dropwise with good stirring. The mixture was stirred for three hours at ambient temperature. Water (250 ml) was added with stirring and the aqueous layer was removed and acidified to a pH of 2–3 with 2N HCl. The organic product was extracted with two 50 ml portions of methylene chloride. The extract was dried over magnesium sulfate and evaporated to dryness. The residue was distilled under reduced pressure (0.2–0.3 mm of Hg) to remove dimethyl malonate (pot temperature 85°–105° C., vapor 35°–39° C.). A gas chromatographic analysis of the residue indicated that it contained 94–97% of the desired product. The oily residue was mixed with 140 ml of water and refluxed for 1.5 hours. The mixture was cooled to room temperature and extracted with two 50 ml portions of methylene chloride. The organic layer was washed with 20 ml portions of 2.4N ammonium hydroxide solution till the aqueous extracts showed a pH of 9. The methylene chloride layer was dried over magnesium sulfate, concentrated to dryness, and triturated with cold n-hexane. The product was collected and dried under vacuum to yield 3.25 g (45-50%) of methyl 2,3,4,5-tetrafluorobenzoylacetate, mp 68°-72° C., which was 98% pure by gas chromatographic analysis. A pure sample was prepared by recrystallization from n-hexane, mp 71°-74° C.

The aqueous basic layer was acidified to pH 2 with 2N HCl. The by-product 2,3,4,5-tetrafluorobenzoic acid was isolated by extraction with methylene chloride to give 1.3 g (26%) as a white crystalline solid, mp 81°-83° C. This was converted to tetrafluorobenzoyl chloride and recycled in the synthesis, Step 2.

We claim:

1. A process for the preparation of a compound of the formula

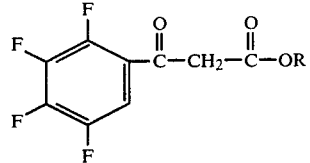

wherein R is a straight or branched alkyl of from one to four carbon atoms; which comprises
   (a) adding a dialkylmalonate to anhydrous sodium methoxide in the presence of toluene and dimethylformamide to produce a slurry containing a corresponding sodium dialkyl malonate;
   (b) adding tetrafluorobenzoylchloride to the above slurry and stirring at 10° to 50° C. for one to four hours forming a corresponding sodium enolate,
   (c) extracting the enolate into water, removing the aqueous layer and acidifying it to a pH of two to three with a strong acid to form a corresponding benzoyl dialkyl malonate,
   (d) hydrolyzing the benzoyl dialkyl malonate with water forming the compound of Formula 1 above,
   (e) isolating and recovering the compound by solvent extraction,
   (f) isolating tetrafluorobenzoic acid, the by-product of the hydrolysis, by solvent extraction, and
   (g) converting it by known means to tetrafluorobenzoylchloride for recycling in step (b) above.

2. The process in claim 1, wherein Step (a) the dialkylmalonate is dimethylmalonate.

3. The process in claim 1, wherein in Step (b) the mixture is stirred for two to three hours at a temperature of 18° to 20° C.

4. The process in claim 1, wherein in step (a) the volume ratio of toluene to dimethylformamide is from 30 to 1 to 70 to 1.

* * * * *